United States Patent
Endo et al.

(10) Patent No.: US 10,159,740 B2
(45) Date of Patent: Dec. 25, 2018

(54) COMPOSITIONS WITH HIGH CONTENT OF SESAMIN CLASS COMPOUNDS

(71) Applicant: SUNTORY HOLDINGS LIMITED, Osaka-shi, Osaka (JP)

(72) Inventors: Shuji Endo, Osaka (JP); Mitsuru Maeda, Osaka (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 0 days.

(21) Appl. No.: 15/104,549

(22) PCT Filed: Dec. 16, 2014

(86) PCT No.: PCT/JP2014/083272
§ 371 (c)(1),
(2) Date: Jun. 15, 2016

(87) PCT Pub. No.: WO2015/093484
PCT Pub. Date: Jun. 25, 2015

(65) Prior Publication Data
US 2016/0310599 A1 Oct. 27, 2016

(30) Foreign Application Priority Data
Dec. 16, 2013 (JP) ................................. 2013-259205

(51) Int. Cl.
| | | |
|---|---|---|
| *A61K 47/28* | (2006.01) | |
| *A23D 9/007* | (2006.01) | |
| *A61K 47/44* | (2017.01) | |
| *A61K 31/36* | (2006.01) | |
| *A61K 31/202* | (2006.01) | |
| *A61K 36/899* | (2006.01) | |
| *A61K 35/60* | (2006.01) | |
| *A23L 33/105* | (2016.01) | |

(52) U.S. Cl.
CPC .............. *A61K 47/28* (2013.01); *A23D 9/007* (2013.01); *A23L 33/105* (2016.08); *A61K 31/202* (2013.01); *A61K 31/36* (2013.01); *A61K 35/60* (2013.01); *A61K 36/899* (2013.01); *A61K 47/44* (2013.01)

(58) Field of Classification Search
CPC ...... A61K 31/36; A61K 35/60; A61K 36/899; A61K 31/202; A61K 47/28; A61K 47/44; A23D 9/007; A23L 33/105; A23V 2250/186; A23V 2250/1862; A23V 2250/1864; A23V 2250/1866; A23V 2250/1868; A23V 2250/187; A23V 2250/1872; A23V 2250/1874; A23V 2250/1876; A23V 2250/1878; A23V 2250/188; A23V 2250/1882; A23V 2250/1884; A23V 2250/1886; A23V 2250/20; A23V 2250/21
USPC ........................................................ 514/464
See application file for complete search history.

(56) References Cited

U.S. PATENT DOCUMENTS

| | | | |
|---|---|---|---|
| 6,172,106 B1 * | 1/2001 | Forse ..................... | A61K 31/36 514/464 |
| 7,288,278 B2 * | 10/2007 | Mellerup ............. | A23D 7/0056 424/439 |
| 7,776,915 B2 * | 8/2010 | Morariu ................... | A61K 8/41 424/401 |
| 8,685,455 B2 * | 4/2014 | Yamada ............... | A61K 9/1075 424/489 |
| 9,408,803 B2 * | 8/2016 | Nakai ...................... | A61K 9/08 |
| 2008/0182894 A1 * | 7/2008 | Takino ................ | A61K 8/0212 514/458 |
| 2013/0237508 A1 * | 9/2013 | Tsuno .................... | A23D 9/007 514/182 |

FOREIGN PATENT DOCUMENTS

| | | |
|---|---|---|
| JP | 2009-073749 A | 4/2009 |
| JP | 2013-163690 A | 8/2013 |
| WO | WO-2013/122122 A1 | 8/2013 |

OTHER PUBLICATIONS

International Search Report dated Feb. 24, 2015 for PCT/JP2014/083272.

* cited by examiner

*Primary Examiner* — My-Chau T. Tran
(74) *Attorney, Agent, or Firm* — Drinker Biddle & Reath LLP

(57) ABSTRACT

The present invention improves the solubility of sesamin-class compounds in fish oil and/or wheat germ oil. More specifically, γ-orizanol is combined with fish oil and/or wheat germ oil as well as sesamin-class compounds.

8 Claims, No Drawings

US 10,159,740 B2

COMPOSITIONS WITH HIGH CONTENT OF SESAMIN CLASS COMPOUNDS

This application is the National Stage of International Application No. PCT/JP2014/083272, filed Dec. 16, 2014, and claims benefit of Japanese Application No. 2013-259205 filed on Dec. 16, 2013.

TECHNICAL FIELD

The present invention relates to the improvement of the solubility of sesamin-class compounds in fish oil and/or wheat germ oil. More particularly, the present invention relates to oil or fat compositions containing fish oil and/or wheat germ oil, sesamin-class compounds, and γ-orizanol.

BACKGROUND ART

The bodily absorption of sesamin-class compounds such as sesamin and episesamin is improved when they are dissolved in oils or fats (Patent Document 1). Therefore, as for designing an oil or fat composition containing sesamin-class compounds, it is important to dissolve sesamin-class compounds as much as possible in the oil or fat composition; however, the solubility of sesamin-class compounds in oils or fats is not necessarily satisfactory.

Regarding this problem, it has been found in Patent Document 1 that triglycerides of middle-chain fatty acids having 8-12 of carbon atoms are capable of dissolving large amounts of sesamin-class compounds.

CITATION LIST

Patent Document

Patent Document 1: JP 2006-306864 A

SUMMARY OF INVENTION

Technical Problem

The present inventors have ascertained that the solubility of sesamin-class compounds in oils or fats, especially in fish oil and/or wheat germ oil, is low. Thus, it is difficult to incorporate high contents of sesamin-class compounds in fish oil and/or wheat germ oil. Furthermore, even if low contents of sesamin-class compounds are incorporated, crystals of sesamin-class compounds are sometimes deposited during storage. Such crystal deposition has a possibility of causing decreased absorption; so there is no choice but to incorporate sesamin-class compounds in fish oil and/or wheat germ oil in amounts that are much lower than their solubilities.

Under these circumstances, the amount of fish oil and/or wheat germ oil that serves as a solvent has to be increased when the amounts of sesamin-class compounds to be ingested at a time are increased. Consequently, one who ingests the oil or fat composition will inevitably take excess calorific value; furthermore, the volume per dosage unit of the oil or fat composition containing sesamin-class compounds is also increased. Especially when the oil or fat composition is prepared as a formulation for oral ingestion, the resulting formulation (e.g. capsule) may become too bulky or too many granules have to be ingested at a time. As a result, troubles might occur during ingestion.

Solution to Problem

The present inventors conducted intensive studies with a view to solving the problems mentioned above and found that when oil or fat compositions containing fish oil and/or wheat germ oil and sesamin-class compounds were combined with γ-orizanol, the solubility of the sesamin-class compounds could be increased. This effect may become prominent when sesamin-class compounds and γ-orizanol are used at specified proportions.

Thus, the present invention relates, but is not limited, to the following:

1. An oil or fat composition containing at least one sesamin-class compound, and at least one γ-orizanol, and fish oil and/or wheat germ oil;
2. The composition according to 1, wherein the ratio of the total weight of the sesamin-class compound to the total weight of the γ-orizanol is between 1:0.05 to 1:100;
3. The composition according to 1 or 2, wherein the weight of the fish oil and/or wheat germ oil is 100 or lower relative to the total weight of the sesamin-class compound which is taken as unity;
4. The composition according to any one of 1 to 3, wherein the sesamin-class compound is sesamin and/or episesamin;
5. The composition according to any one of 1 to 4, wherein the γ-orizanol is contained in the form of rice germ oil;
6. The composition according to any one of 1 to 5, which is a food or a beverage;
7. The food or beverage according to 6, which has a function label indicating that at least one ingredient selected from the group consisting of the sesamin-class compound, γ-orizanol, and fish oil is an ingredient having a health-promoting function (active ingredient);
8. The composition according to any one of 1 to 7, which is an anti-oxidant, agent of preventing or improving hyperlipidemia, agent of improving hepatic function, agent of preventing or improving hypertension, agent of preventing drunken sickness, agent of preventing aging, anti-fatigue agent, agent of lowering blood LDL cholesterol, agent of lowering blood neutral lipid, agent of preventing thrombosis, agent of preventing arteriosclerosis, agent of improving learning capacity or memory, agent of preventing senile dementia, agent of protecting gastric mucosa, agent of regulating endocrine, agent of controlling autonomic nerve, agent of preventing or improving psychophysiologic disorders, agent of maintaining cardiac function, agent of improving blood stream, agent of suppressing platelet aggregation, agent of improving vascular endothelial function, agent of maintaining visual function, agent of improving stress symptoms, agent of improving depressive symptoms, agent of improving posttraumatic stress disorders, stamina improver, agent of producing energy, agent of preventing frailty (debility due to aging), agent of maintaining skin health, agent of maintaining hair health, or agent of extending longevity;
9. The food or beverage according to 6 or 7, which has a label indicating that it is to be used for preventing biooxidation, preventing or improving hyperlipidemia, improving hepatic function, preventing or improving hypertension, preventing drunken sickness, preventing aging, preventing or improving fatigue, lowering blood LDL cholesterol, lowering blood neutral lipid, preventing thrombosis, preventing arteriosclerosis, improving learning capacity or memory, preventing senile dementia, protecting gastric mucosa, regulating endocrine, regulating autonomic nerve, preventing or improving psychophysiologic disorders, maintaining cardiac function, improving blood stream, suppressing platelet aggregation, improving vascular endothelial function, maintaining visual function, improving stress disorders, improving depressive symptoms, improving posttraumatic stress disorders, improving stamina, producing energy, preventing frailty (debility due to aging), maintaining skin health, maintaining hair health, or extending longevity;

10. Use of the composition according to any one of 1 to 7 as an anti-oxidant, agent of preventing or improving hyperlipidemia, agent of improving hepatic function, agent of preventing or improving hypertension, agent of preventing drunken sickness, agent of preventing aging, anti-fatigue agent, agent of lowering blood LDL cholesterol, agent of lowering blood neutral lipid, agent of preventing thrombosis, agent of preventing arteriosclerosis, agent of improving learning capacity or memory, agent of preventing senile dementia, agent of protecting gastric mucosa, agent of regulating endocrine, agent of controlling autonomic nerve, agent of preventing or improving psychophysiologic disorders, agent of maintaining cardiac function, agent of improving blood stream, agent of suppressing platelet aggregation, agent of improving vascular endothelial function, agent of maintaining visual function, agent of improving stress symptoms, agent of improving depressive symptoms, agent of improving posttraumatic stress disorders, stamina improver, agent of producing energy, agent of preventing frailty (debility due to aging), agent of maintaining skin health, agent of maintaining hair health, or agent of extending longevity;

11. A method comprising administering to a subject the composition according to any one of 1 to 7 for preventing biooxidation, preventing or improving hyperlipidemia, improving hepatic function, preventing or improving hypertension, preventing drunken sickness, preventing aging, preventing or improving fatigue, lowering blood LDL cholesterol, lowering blood neutral lipid, preventing thrombosis, preventing arteriosclerosis, improving learning capacity or memory, preventing senile dementia, protecting gastric mucosa, regulating endocrine, regulating autonomic nerve, preventing or improving psychophysiologic disorders, maintaining cardiac function, improving blood stream, suppressing platelet aggregation, improving vascular endothelial function, maintaining visual function, improving stress disorders, improving depressive symptoms, improving posttraumatic stress disorders, improving stamina, producing energy, preventing frailty (debility due to aging), maintaining skin health, maintaining hair health, or extending longevity in the subject;

12. A method for improving the solubility of a sesamin-class compound in a oil or fat composition containing at least one sesamin-class compound and fish oil and/or wheat germ oil, which comprises incorporating γ-orizanol in the composition, and;

13. The method according to 12, which comprises incorporating γ-orizanol in the form of rice germ oil in the composition.

Advantageous Effects of Invention

The present invention can improve the solubility of sesamin-class compounds in fish oil and/or wheat germ oil. Hence, the volume of the oil or fat composition containing sesamin-class compounds is sufficiently decreased to facilitate its ingestion. Furthermore, the present invention can suppress crystal deposition in the oil or fat composition during preservation and thereby can increase its storage stability. Note that these facts do not mean that the oil or fat composition of the present invention necessarily features complete dissolution of the sesamin-class compounds.

DESCRIPTION OF EMBODIMENTS

The term "oil or fat composition" in the present invention refers to an oil or fat that may contain ingredients other than oils or fats. Hence, the oil or fat composition of the present invention refers to a fat or oil containing at least one sesamin-class compound, and at least one γ-orizanol, and fish oil and/or wheat germ oil which is an oil or fat component. Ingredients such as sesamin-class compounds, γ-orizanol, etc. are preferably dissolved in the oil or fat, but they may partially remain undissolved.

Sesamin-Class Compounds

The term "sesamin-class compounds" as used in connection with the present invention is the collective term for a series of compounds including sesamin and their analogs. Examples of the sesamin analogs include episesamin and dioxabicyclo[3.3.0]octane derivatives as disclosed in JP 4-9331 A. Specific examples of the sesamin-class compounds include sesamin, episesamin, sesaminol, episesaminol, sesamolin, etc., and the stereoisomers or racemic bodies of these compounds may be used either independently or in admixture; however, in the present invention, sesamin and/or episesamin can be used with advantage.

The sesamin-class compounds to be used in the present invention are not limited in any way by their form, production methods, and the like. If, for example, sesamin is chosen as the sesamin-class compound, sesame oil may be subjected to extraction by a known method (such as the one described in JP 4-9331 A) to obtain sesamin (hereinafter called a sesamin extract or concentrate), which is then used; if desired, a commercial grade of sesame oil (in liquid form) may be used as such. However, one disadvantage of using sesame oil is its low sesamin content (usually less than 1%), so if one attempts to incorporate sesamin in the amount required to attain its physiological actions, the volume per unit dosage of the composition to be prescribed becomes so excessive as to cause occasional inconvenience to ingestion. In particular, in the case where the composition is formulated for oral administration, the preparation becomes so bulky as to cause trouble in ingestion. Hence, for the specific reason that the composition need be ingested in a smaller amount, the sesamin extract (or sesamin concentrate) from sesame oil is preferably used. It should be noted here that since the characteristic flavor of sesame oil is sometimes evaluated to be organoleptically undesirable, the sesamin extract (or sesamin concentrate) may be rendered tasteless and odorless by a known means such as treatment with activated clay.

The amount of the sesamin-class compound contained in the oil or fat composition is not particularly limited, but it is typically 0.1% to 10.0% by weight, preferably 0.2% to 5.0% by weight.

The content of the sesamin-class compound can be measured using any known methods including HPLC method. Regarding HPLC method, for example, the method described in the official gazette of JP 2009-155312 A and the like can be referenced.

γ-Orizanol

The important component for improving the solubility of sesamin-class compounds is γ-orizanol. It is known that γ-orizanol has various physiological actions including the action for lowering blood neural lipid (Geriant.mad. 19, 1812-1840, 1981), the action for regulating endocrine and autonomic nerve (Folia Pharmacologica Japonica, 75(4), 399-403, 1979), and the action for protecting gastric mucosa (Folia Pharmacologica Japonica, 84(6), 537-542, 1984); and purified γ-orizanol is approved as pharmaceuticals such as therapeutic agents for hyperlipidemia and therapeutic agents for psychophysiologic disorders (e.g. menopausal symptom and irritable bowel syndrome). The term "γ-orizanol" as used with regard to the present invention is the collective term for compounds comprising ferulic acid to which triterpene alcohols or plant sterols are attached via ester bond. Examples of the triterpene alcohols include, for example, cycloartenol, 24-methylenecycloartanol, cycloartanol, and cyclobranol; and the plant sterols can be exemplified by campesterol, stigmasterol, β-sitosterol, and the like. In the present invention, these compounds may be used independently or in admixture.

It is known that γ-orizanol is contained in brown rice, corn, barley, etc. γ-orizanol is also contained in rice bran oil that is extracted from brown rice. Furthermore, γ-orizanol is also contained in rice germ oil. Rice germ oil is an oil extracted from the germ of rice and established knowledge is that it usually contains about 1.0% to 1.5% w/w of γ-orizanol.

The γ-orizanol to be used in the present invention is in no way limited by its origin, form, methods of production, and the like. For example, purified γ-orizanol may be used; any commercially available rice germ oil and the like may be used as such; a concentrate with a high content of γ-orizanol may be used; and combinations thereof may also be used. The concentrate of γ-orizanol is commercially available; Rice Germ Oil Gamma 30 (Tsuno Co., Ltd.), γ-orizanol, Orizadrim V-50, Rice Bran Oil, and Brown Rice Germ Oil (Oriza Oil & Fat Chemical Co., Ltd.) are given as examples of such concentrate.

The amount of the γ-orizanol contained in the oil or fat composition is not particularly limited but a typical value is 0.05% to 20% by weight.

As a method for determining the amount of γ-orizanol, a known method such as UV absorbance method or HPLC method can be employed as appropriate. For example, as described in "Japanese Standards of Quasi-drug Ingredients" and "Voluntary Standards of Food Additives other than Chemical Synthetics," quantitative determination can be performed by dissolving a sample into heptane and then measuring the absorbance at its absorption maximum wavelength in the vicinity of 315 nm.

Fish Oil

The term "fish oil" as used in connection with the present invention refers to an oil or fat that is obtained from fish. The chief ingredient of fish oil is usually a triglyceride which is constituted of fatty acids such as docosahexaenoic acid (DHA), eicosapentaenoic acid (EPA), docosapentaenoic acid (DPA), eicosatetraenoic acid or the like; in addition, the fish oil may contain various free fatty acids, cholesterols, etc.

The fish oil to be used in the present invention is in no way limited by its origin, method of production, and the like. For example, the fish oil may be sardine oil, tuna oil, saury oil, herring oil, or mackerel oil.

In the present invention, crude fish oil or purified fish oil may be used, but purified fish oil is preferably used. The contents of free fatty acids and cholesterols are low in purified fish oil. As the purified fish oil, DHA-22, DHA-22K, DHA-22HG, DHA-KHG, DHA-46A, DHA-50, DHA-70, DHA-27W, DHA-46MK, EPA-18MN, EPA-28MN, EPA-28MNSP-E(M) (products of Maruha Nichiro Corporation), DHA-27, DHA-46A, DHA-55, DHA-70 (products of Nippon Suisan Kaisha, Ltd.), and the like can be used.

The fish oil to be used in the present invention may consist of a single kind of oil or fat, or a mixture of two or more oils or fats.

Wheat Germ Oil

The term "wheat germ oil" as used in connection with the present invention refers to an oil that is obtained from the germ of wheat. Methods for producing wheat germ oil have been well established; furthermore, wheat germ oils are easily available as commercial products.

The amount of the fish oil and/or the wheat germ oil in the oil or fat composition is not particularly limited, but a typical value is 30% to 99% by weight, preferably 40% to 80% by weight.

The Proportions of Respective Ingredients

In the present invention, the improvement of the solubility of the sesamin-class compound becomes prominent when the sesamin-class compound and the γ-orizanol are present at specified proportions. The ratio between the total weight of the sesamin-class compound and the total weight of the γ-orizanol in the composition of the present invention is preferably 1:0.05 to 1:100, more preferably 1:0.05 to 1:10, more preferably 1:0.1 to 1:10, more preferably 1:0.2 to 1:5, and even more preferably 1:0.25 to 1:1.3.

The weight of the fish oil and/or wheat germ oil in the composition of the present invention as relative to the total weight of the sesamin-class compound which is taken as unity is preferably 100 or less, more preferably 95 or less, more preferably 90 or less, and even more preferably 80 or less. The weight of the fish oil and/or wheat germ oil relative to the total weight of the sesamin-class compound which is taken as unity is typically 1 or more, 10 or more, 20 or more, or 30 or more. The weight of the fish oil and/or wheat germ oil relative to the total weight of the sesamin-class compound which is taken as unity may be within the numerical ranges that are determined by any combinations of the above-noted upper limits and lower limits. For example, the value of interest may be within the range of 1 to 100, 1 to 95, 10 to 90, 20 to 80, or 30 to 80. Alternatively, the corresponding ratio may be from 1:35 to 1:47.

Other Ingredients

In addition to the fish oil, wheat germ oil, sesamin-class compound, and γ-orizanol, any ingredients may be incorporated as appropriate in the composition of the present invention as long as the effects of the composition are not impaired. For example, vitamins such as vitamin E and vitamin C, minerals, nutrient components, flavors, antiseptics, stabilizers, anti-oxidants, etc. can be incorporated as appropriate.

Applications

The composition of the present invention is expected to exhibit various health-promoting functions (or physiological actions) that are possessed by the sesamin-class compound, fish oil, wheat germ oil, and γ-orizanol; hence, it can be utilized with advantage as, for example, health foods, functional foods (including foods for specified health uses (FOSHU), qualified FOSHU, and foods with nutrient function claims (FNFC)), as well as foods for special dietary uses, dietary supplement, and the like. In addition, the composition of the present invention can be used in processed oil and fat foods as well as in common edible oils or fats. The processed oil and fat foods as mentioned here refer to the above-noted oil or fat compositions to which other food ingredients have been added, followed by subsequent processing.

The forms in which the composition of the present invention is utilized are not particularly limited; the composition of the present invention can be used in the form of capsules, candies, drops, and the like. For example, the composition of the present invention can be used as an internal composition of capsules (especially, soft capsules).

The oil or fat composition of the present invention exerts various health-promoting functions (or physiological actions) arising from ingredients with health claims (functional substances) such as the sesamin-class compound, γ-orizanol, and fish oil (more specifically DHA and EPA) which are components of the composition. The ingredients having health-promoting functions (active ingredients) as described herein refer to those ingredients which prove useful for maintaining and promoting health when they are ingested in certain amounts. Hence, the composition of the present invention may be used for applications that are derived from such ingredients having health-promoting functions.

In another aspect, the present invention relates, for example, to oil or fat compositions, especially foods or beverages, containing at least one sesamin-class compound, and at least one γ-orizanol, and fish oil and/or wheat germ oil, which are anti-oxidants, agents of preventing or improving hyperlipidemia, agents of improving hepatic function, agents of preventing or improving hypertension, agents of preventing drunken sickness, agents of preventing aging, anti-fatigue agents, agents of lowering blood LDL cholesterol, agents of lowering blood neutral lipid, agents of preventing thrombosis, agents of preventing arteriosclerosis, agents of improving learning capacity or memory, agents of preventing senile dementia, agents of protecting gastric mucosa, agents of regulating endocrine, agents of controlling autonomic nerve, agents of preventing or improving psychophysiologic disorders, agents of maintaining cardiac function, agents of improving blood stream, agents of suppressing platelet aggregation, agents of improving vascular endothelial function, agents of maintaining visual function, agents of improving stress symptoms, agents of improving depressive symptoms, agents of improving posttraumatic stress disorders, stamina improvers, agents of producing energy, agents of preventing frailty (debility due to aging), agents of maintaining skin health, agents of maintaining hair health, or agents of extending longevity.

In another aspect, the present invention relates to oil or fat compositions, especially foods or beverages, containing at least one sesamin-class compound, and at least one γ-orizanol, and fish oil and/or wheat germ oil, which are for preventing biooxidation, preventing or improving hyperlipidemia, improving hepatic function, preventing or improving hypertension, preventing drunken sickness, preventing aging, preventing or improving fatigue, lowering blood LDL cholesterol, lowering blood neutral lipid, preventing thrombosis, preventing arteriosclerosis, improving learning capacity or memory, preventing senile dementia, protecting gastric mucosa, regulating endocrine, regulating autonomic nerve, preventing or improving psychophysiologic disorders, maintaining cardiac function, improving blood stream, suppressing platelet aggregation, improving vascular endothelial function, maintaining visual function, improving stress disorders, improving depressive symptoms, improving posttraumatic disorders, improving stamina, producing energy, preventing frailty (debility due to aging), maintaining skin health, maintaining hair health, or extending longevity.

In another aspect, the present invention relates to oil or fat compositions, especially foods or beverages, containing at least one sesamin-class compound, and at least one γ-orizanol, and fish oil and/or wheat germ oil, which have a label indicating that they are to be used for preventing biooxidation, preventing or improving hyperlipidemia, improving hepatic function, preventing or improving hypertension, preventing drunken sickness, preventing aging, preventing or improving fatigue, lowering blood LDL cholesterol, lowering blood neutral lipid, preventing thrombosis, preventing arteriosclerosis, improving learning capacity or memory, preventing senile dementia, protecting gastric mucosa, regulating endocrine, regulating autonomic nerve, preventing or improving psychophysiologic disorders, maintaining cardiac function, improving blood stream, suppressing platelet aggregation, improving vascular endothelial function, maintaining visual function, improving stress disorders, improving depressive symptoms, improving posttraumatic disorders, improving stamina, producing energy, preventing frailty (debility due to aging), maintaining skin health, maintaining hair health, or extending longevity. In the present specification, the above-noted label and other labels such as health claims may be attached to the composition itself, or to the container or package of the composition.

In another aspect, the present invention relates to the use of oil or fat compositions, especially foods or beverages, containing at least one sesamin-class compound, and at least one γ-orizanol, and fish oil and/or wheat germ oil, as anti-oxidants, agents of preventing or improving hyperlipidemia, agents of improving hepatic function, agents of preventing or improving hypertension, agents of preventing drunken sickness, agents of preventing aging, anti-fatigue agents, agents of lowering blood LDL cholesterol, agents of lowering blood neutral lipid, agents of preventing thrombosis, agents of preventing arteriosclerosis, agents of improving learning capacity or memory, agents of preventing senile dementia, agents of protecting gastric mucosa, agents of regulating endocrine, agents of controlling autonomic nerve, agents of preventing or improving psychophysiologic disorders, agents of maintaining cardiac function, agents of improving blood stream, agents of suppressing platelet aggregation, agents of improving vascular endothelial function, agents of maintaining visual function, agents of improving stress symptoms, agents of improving depressive symptoms, agents of improving posttraumatic stress disorders, stamina improvers, agents of producing energy, agents of preventing frailty (debility due to aging), agents of maintaining skin health, agents of maintaining hair health, or agents of extending longevity. The above-described use is preferably a non-medical use.

In another aspect, the present invention relates to a method for preventing biooxidation, preventing or improving hyperlipidemia, improving hepatic function, preventing or improving hypertension, preventing drunken sickness, preventing aging, preventing or improving fatigue, lowering blood LDL cholesterol, lowering blood neutral lipid, preventing thrombosis, preventing arteriosclerosis, improving learning capacity or memory, preventing senile dementia, protecting gastric mucosa, regulating endocrine, regulating autonomic nerve, preventing or improving psychophysiologic disorders, maintaining cardiac function, improving blood stream, suppressing platelet aggregation, improving vascular endothelial function, maintaining visual function, improving stress disorders, improving depressive symptoms, improving posttraumatic disorders, improving stamina, producing energy, preventing frailty (debility due to aging), maintaining skin health, maintaining hair health, or extending longevity in a subject, which comprises administering a subject with oil or fat compositions, especially foods or beverages, containing at least one sesamin-class compound, at least one γ-orizanol, and fish oil and/or wheat germ oil. The subject to be administered with the composition includes mammals such as humans which require the enhancement of the bodily absorption as described above.

The ratios, proportions, etc. of the sesamin-class compound, γ-orizanol, fish oil, and wheat germ oil to be used in the present invention can be determined as appropriate depending on the numerical values that are described above with regard to the oil or fat compositions. The same applies to the types of the sesamin-class compound, γ-orizanol, fish oil, and wheat germ oil to be used.

The sesamin-class compound may exhibit the anti-oxidant action, the action of preventing or improving hyperlipidemia, the action of improving hepatic function, the action of preventing or improving hypertension, the action of preventing drunken sickness, the action of preventing aging, and the anti-fatigue action. For example, refer to WO 2006/106926.

DHA and EPA may exhibit the action of preventing or improving hyperlipidemia, the action of lowering blood LDL cholesterol, the action of lowering blood neutral lipid, the action for preventing thrombosis, the action of preventing arteriosclerosis, the action of improving learning capacity or memory, the action of preventing senile dementia, and the action of maintaining cardiac function. For example, refer to the patent gazette of JP 2007-89522 A.

The γ-orizanol may exhibit the action of protecting gastric mucosa, the action of regulating endocrine, the action of regulating autonomic nerve, the action of preventing or improving psychophysiologic disorders.

By using an anti-oxidant, the anti-oxidant action can be exerted in the body (the action of preventing biooxidation). Examples of the anti-oxidant include agents for scavenging active oxygen in vivo, agents for inhibiting the generation of lipid peroxides in vivo, etc. The prevention of biooxidation and the anti-oxidant can be described by phrases such as "the preventing or inhibiting (agent) of rusting of the body" and "the body's rust remover (ingredient)."

The anti-oxidants are also useful as agents for preventing aging and anti-fatigue agents. The preventing of aging includes preventing the aging of skin. The anti-fatigue agents of the present invention refer to compositions for preventing or improving fatigue, which include compositions for reducing or recovering from fatigue. The "fatigue" as used in the present invention refers to phenomena in which physical or mental performance is temporarily lowered when physical or mental burdens are continuously applied. In addition, the "fatigue" as used in the present invention includes chronic fatigue syndrome and fatigue death. The (agents for) preventing aging, anti-fatigue agents, and preventing or improving fatigue can be described by phrases such as "(ingredients) for leading youthful life," "(ingredients) for becoming youthful," and "(ingredients) for maintaining or recovering youthfulness."

The (agents for) preventing or improving hyperlipidemia, the (agents for) lowering blood LDL cholesterol, the (agents for) lowering blood neutral lipid, and the (agents for) preventing thrombosis can be described by phrases such as "(ingredients) for improving the viscosity of (sticky) blood." Note that thrombosis includes cerebral infarction, myocardial infarction, etc.

The (agents for) improving learning capacity or memory and the (agents for) preventing senile dementia can be described by phrases such as "the (agents for) maintaining brain power."

The (agents for) maintaining cardiac function can be described by phrases such as "(ingredients) for the smooth functioning of heart."

The Improvement of the Solubility of Sesamin-Class Compounds

In another aspect, the present invention is directed to a method for improving the solubility of a sesamin-class compound in a oil or fat composition containing at least one sesamin-class compound and fish oil and/or wheat germ oil, which comprises incorporating γ-orizanol in the composition. The method further comprises, preferably, the step of adjusting the ratio between the total weights of the sesamin-class compound and the γ-orizanol in the oil or fat composition. The ratio is preferably 1:0.05 to 1:100, more preferably 1:0.05 to 1:10, more preferably 1:0.1 to 1:10, more preferably 1:0.2 to 1:5, even more preferably 1:0.25 to 1:1.3.

It suffices for the present invention to contain γ-orizanol in the eventually obtained oil or fat composition. It also suffices that the ratio between the amounts of sesamin and γ-orizanol in the eventually obtained oil or fat composition falls within the desired range. Hence, the means for incorporating the γ-orizanol and the means for adjusting the proportion of the respective ingredients are not limited and any methods known to those skilled in the art can be employed. In addition, the timing at which these methods are performed is not limited. For example, it is possible to add the γ-orizanol before, during, or after any of the steps for producing the oil or fat composition.

EXAMPLES

The present invention is described in greater detail by means of the following examples, to which the present invention is in no way limited.

Example 1

<The Method of Crystal Deposition>

Sesamin was added to either DHA-containing purified fish oil (DHA-55; Nippon Suisan Kaisha, Ltd.) or wheat germ oil (Summit Oil Mill, Co., Ltd.) in the amounts indicated in Table 1A, 1B, or 2 in order to prepare test samples and comparative samples. To the test samples, either γ-orizanol (Wako Pure Chemical Industries, Ltd.) or Rice Germ Oil Gamma 30S (Tsuno Co., Ltd.) was further added in the amounts indicated in Table 1A, 1B, or 2. Rice Germ Oil Gamma 30S was used in such amounts that γ-orizanol was provided in 50 or 200 mg.

The weight of each test sample or comparative sample was adjusted to be 10 g in total using oils as solvents, and the samples were heated to 85° C. to make sesamin dissolved completely and then stored at 5° C. for a week. Each liquid sample containing crystal deposits was subjected to suction filtration to perform solid-liquid separation, and ethanol was added to the resulting crystals in order to wash out the oils. The weights of the crystals obtained by these operations were measured. Table 1A, 1B, and 2 show the weights of the crystals from each test sample.

TABLE 1A

| Sample | Fish oil | Sesamin | γ-orizanol | Rice Germ Oil Gamma 30S | Crystal |
|---|---|---|---|---|---|
| Comparison 1 | 9800 | 200 | 0 | — | 3.1 |
| Test 1 | 9780 | 200 | 20 | — | 0 |
| Test 2 | 9750 | 200 | 50 | — | 0.6 |
| Test 3 | 9700 | 200 | 100 | — | 0.9 |
| Test 4 | 9600 | 200 | 200 | — | 1.0 |

*The amount of each component is in mg.

TABLE 1B

| Sample | Fish oil | Sesamin | γ-orizanol | Rice Germ Oil Gamma 30S | Crystal |
|---|---|---|---|---|---|
| Comparison 2 | 9700 | 300 | 0 | — | 99.7 |
| Test 5 | 9650 | 300 | 50 | — | 69.2 |
| Test 6 | 9600 | 300 | 100 | — | 49.5 |

TABLE 1B-continued

| Sample | Fish oil | Sesamin | γ-orizanol | Rice Germ Oil Gamma 30S | Crystal |
|---|---|---|---|---|---|
| Test 7 | 9500 | 300 | 200 | — | 45.4 |
| Test 8 | 9533 | 300 | (50) | 167 | 67.1 |
| Test 9 | 9033 | 300 | (200) | 667 | 41.5 |
| Test 10 | 9300 | 300 | 400 | — | 53.6 |

*The amount of each component is in mg.

TABLE 2

| Sample | Wheat germ oil | Sesamin | γ-orizanol | Crystal |
|---|---|---|---|---|
| Comparison 3 | 9800 | 200 | 0 | 59.5 |
| Test 11 | 9700 | 200 | 100 | 31.8 |
| Test 12 | 9600 | 200 | 200 | 42.7 |

*The amount of each component is in mg.

The crystal deposits were subjected to the following analyses and, as a result, all were considered to be made up of sesamin.

<The Method of Measuring the Purity of Crystals>

This measurement method can determine the content of orizanol in the crystal deposits.

8 mg of γ-orizanol (standard product of cycloartenyl ferulate; Wako Pure Chemical Industries, Ltd.) was measured in a volumetric flask and heptane was added to make 100 mL. Aside from this solution, 8 mg of the crystals obtained from each sample was measured and heptane was added to make 100 mL. After dissolving by sonication, 10-fold dilution was conducted to make a liquid for measurement. Subsequently, each liquid was measured for its absorbance (315 nm).

<Discussion>

The foregoing results revealed that γ-orizanol could increase the solubility of the sesamin-class compound in the fish oil and/or wheat germ oil. In addition, the solubility of the sesamin-class compound was increased more by using a rice germ oil solution of γ-orizanol than by using γ-orizanol on its own.

(Formulation 1) Capsule

| Gelatin | 60.0% |
|---|---|
| Glycerin | 30.0% |
| Methyl paraoxybenzoate | 0.15% |
| Propyl paraoxybenzoate | 0.51% |
| Water | q.s. |

A soft capsule shell made of the above ingredients was filled by the usual method with the following oil or fat composition in which sesamin-class compounds were dissolved, whereby soft capsules were obtained.

| Sesamin (sesamin:episesamin = 1:1) | 10 mg |
|---|---|
| Glycerol fatty acid ester | 15.0 mg |
| Beeswax | 15.0 mg |
| γ-orizanol | 1.0, 2.0, 2.5, 13.0, 50.0 or 100.0 mg |
| Fish oil | 1000 mg |

(Formulation 2) Capsule

The soft capsule shell as in Formulation 1 was filled by the usual method with the following oil or fat composition in which sesamin-class compounds were dissolved, whereby soft capsules were obtained.

| Sesamin (sesamin:episesamin = 1:1) | 10 mg |
|---|---|
| Glycerol fatty acid ester | 15.0 mg |
| Beeswax | 15.0 mg |
| γ-orizanol | 1.0, 2.0, 2.5, 13.0, 50.0 or 100.0 mg |
| Wheat germ oil | 500 mg |

(Formulation 3) Capsule

The soft capsule shell as in Formulation 1 was filled by the method with the following oil or fat composition in which sesamin-class compounds were dissolved, whereby soft capsules were obtained.

| Sesamin (sesamin:episesamin = 1:1) | 10 mg |
|---|---|
| Glycerol fatty acid ester | 15.0 mg |
| Beeswax | 15.0 mg |
| Rice Germ Oil Gamma 30S | (in a sufficient amount to provide 1.0, 2.0, 2.5, 13.0, 50.0 or 100.0 mg of γ-orizanol) |
| Fish oil | 500 mg |

(Formulation 4) Capsule

The soft capsule shell as in Formulation 1 was filled by the usual method with the following oil or fat composition in which sesamin-class compounds were dissolved, whereby soft capsules were obtained.

| Sesamin (sesamin:episesamin = 1:1) | 10 mg |
|---|---|
| Glycerol fatty acid ester | 15.0 mg |
| Beeswax | 15.0 mg |
| Rice Germ Oil Gamma 30S | (in a sufficient amount to provide 1.0, 2.0, 2.5, 13.0, 50.0 or 100.0 mg of γ-orizanol) |
| Wheat germ oil | 1000 mg |

Finally, the following remarks are given for the purpose of clarification; the numerical ranges represented by the upper and lower limits in the present specification, i.e. "from a lower limit to an upper limit," are inclusive of the indicated lower and upper limits. For example, a range represented as "1 to 2" includes 1 and 2. The same applies to the respective numerical values for proportions.

The invention claimed is:

1. An oil or fat composition containing at least one sesamin-class compound, at least one γ-orizanol, and a fish oil, wherein a ratio of the total weight of all sesamin-class compounds to the fish oil is 1:1 to 1:100, and wherein all sesamin-class compounds and all γ-orizanols are in a weight ratio of between 1:0.1 to 1:1.3 by total weight composition weight.

2. The composition according to claim 1, wherein the at least one sesamin-class compound is sesamin and/or episesamin.

3. The composition according to claim 1, wherein the at least one γ-orizanol is from rice germ oil.

4. A food or a beverage comprising the composition of claim 1.

5. A method of improving the solubility of at least one sesamin-class compound, comprising combining the at least one sesamin-class compound, at least one γ-orizanol, and a fish oil, wherein a ratio of the total weight of all sesamin-class compounds to the fish oil is 1:1 to 1:100, and wherein all sesamin-class compounds and all γ-orizanols are in a weight ratio of between 1:0.1 to 1:1.3 by total weight composition weight.

6. The method according to claim 5, wherein the at least one γ-orizanol is from rice germ oil.

7. The composition according to claim 1, wherein all sesamin-class compounds are 0.1% to 10.0% by composition weight; wherein all γ-orizanol is 0.05% to 20% by composition weight; and wherein the fish oil in the composition is 30% to 99% by weight.

8. A method comprising administering to a subject the composition according to claim 1, for improving biooxidation, improving hyperlipidemia, improving hepatic function, preventing or improving hypertension, treating drunken sickness, preventing aging, improving fatigue, lowering blood LDL cholesterol, lowering blood neutral lipid, treating thrombosis, preventing arteriosclerosis, improving learning capacity or memory, preventing senile dementia, protecting gastric mucosa, regulating endocrine, regulating autonomic nerve, improving psychophysiologic disorders, maintaining cardiac function, improving blood stream, suppressing platelet aggregation, improving vascular endothelial function, maintaining visual function, improving stress disorders, improving depressive symptoms, improving posttraumatic stress disorders, improving stamina, producing energy, improving frailty, maintaining skin health, maintaining hair health, or extending longevity in the subject.

* * * * *